(12) United States Patent
Ebel et al.

(10) Patent No.: US 9,073,826 B2
(45) Date of Patent: Jul. 7, 2015

(54) PROCESS FOR PREPARING AND PURIFYING SALTS OF ACRYLAMIDO-2-METHYLPROPANESULFONIC ACID

(71) Applicant: BASF SE, Ludwigshafen (DE)

(72) Inventors: Klaus Ebel, Lampertheim (DE); Tobias Voitl, Schifferstadt (DE); Andreas Keller, Speyer (DE); Stefan Rüdenauer, Worms (DE); Karsten Bartling, Neustadt (DE); Bjorn Langlotz, Trostberg (DE); Jochen Steiner, Bensheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/687,156

(22) Filed: Nov. 28, 2012

(65) Prior Publication Data

US 2013/0137893 A1 May 30, 2013

Related U.S. Application Data

(60) Provisional application No. 61/564,327, filed on Nov. 29, 2011.

(51) Int. Cl.
*C07C 303/22* (2006.01)
*C07C 309/15* (2006.01)
(Continued)

(52) U.S. Cl.
CPC ............. *C07C 303/22* (2013.01); *C07C 309/15* (2013.01); *C07C 303/32* (2013.01); *C07C 303/44* (2013.01)

(58) Field of Classification Search
None
See application file for complete search history.

(56) References Cited

U.S. PATENT DOCUMENTS 4,337,215 A 6/1982 Doi et al.

4,650,614 A * 3/1987 Jevne et al. .................... 562/105
(Continued)

FOREIGN PATENT DOCUMENTS

| JP | H-0377860 A | 4/1991 |
|---|---|---|
| JP | 2004-143078 A | 5/2004 |

(Continued)

OTHER PUBLICATIONS

Kirk-Othmer Encyclopedia of Chemical Technology Copyright © 2002 by John Wiley & Sons, Inc., pp. 95-147, Article Online Posting Date: Aug. 16, 2002.*

(Continued)

*Primary Examiner* — Karl J Puttlitz
(74) *Attorney, Agent, or Firm* — Drinker Biddle & Reath LLP

(57) ABSTRACT

A process for preparing salts of acrylamido-2-methylpropanesulfonic acid (A) using the steps of:
preparing a solution of a contaminated salt of acrylamido-2-methyl-propanesulfonic acid (A) in an anhydrous organic solvent (L) using at least one basic component (B) selected from the group of alkali metal oxides, alkaline earth metal oxides, alkali metal hydroxides, alkaline earth metal hydroxides and amines of the formula (I)

$$NR_aR_bR_c \quad (I)$$

where the Ra, Rb and Rc radicals are each independently:
hydrogen, C1-C4-alkyl, hydroxy-C1-C4-alkyl or C1-C4-alkoxy,
where the molar ratio of compound (A) to the basic component (B) is 1:1 to 1:3,
recovering the dissolved salt of compound (A) by crystallization or by precipitation, by altering the temperature and/or the pressure and/or the concentration of the salt in the solution. This leads to salts which are low in by-products and are particularly suitable for polymerization.

14 Claims, 2 Drawing Sheets

(51) Int. Cl.
*C07C 303/32* (2006.01)
*C07C 303/44* (2006.01)

(56) References Cited

U.S. PATENT DOCUMENTS

| | | |
|---|---|---|
| 4,701,283 A | 10/1987 | Itoh et al. |
| 6,331,647 B1 | 12/2001 | Quinn et al. |
| 2010/0274048 A1 | 10/2010 | Wakayama |

FOREIGN PATENT DOCUMENTS

| | | | |
|---|---|---|---|
| JP | 2004143078 | * | 5/2004 |
| RO | 104626 B1 | | 9/1994 |
| WO | WO-2011/025847 A2 | | 3/2011 |

OTHER PUBLICATIONS

"Crystallization and Precipitation" in Ullmann's Encyclopedia of Industrial Chemistry, Copyright © 2002 by Wiley-VCH Verlag GmbH & Co. KGaA, pp. 1-51.*

Rouhi, "The Right Stuff, from research and development to the clinic, getting drug crystals right is full of pitfalls", Chemical & Engineering News, Feb. 24, 2003, pp. 32-35.*

Machine Translation of JP 2004143078.*

Kurenkov, V. F., et al., "Copolymerization of Acrylamide with Salts of 2-Acrylamido-2-Methylpropanesulfic Acid in Aqueous Solutions as Influenced by the Nature of Double-Charged Cation", Russian Journal of Applied Chemistry, vol. 74, No. 5, (2001), pp. 813-817.

International Search Report for PCT/EP2012/073791 dated Jun. 28, 2013.

"Purification of 2-acrylamide-2-methylpropanesulfonic acid", XP002698776, Database accession No. 608826 (citation JP 3077860), dated 1991.

XP00269877, Database Accession No. 434131 (accompanied citation JP20020309707), dated 2004.

* cited by examiner

PROCESS FOR PREPARING AND PURIFYING SALTS OF ACRYLAMIDO-2-METHYLPROPANESULFONIC ACID

CROSS-REFERENCE TO RELATED APPLICATIONS

This application claims benefit (under 35 USC 119(e)) of U.S. Provisional Application 61/564,327, filed Nov. 29, 2011, which is incorporated by reference.

The invention relates to a process for preparing salts of acrylamido-2-methylpropanesulfonic acid free of by-products or low in by-products (hereinafter, ®AMPS or compound A). The invention relates more particularly to the preparation of sodium salt of compound A with a purity of at least 99%, especially at least 99.5%.

To date, purified salts of compound (A) have been prepared using acrylamido-2-methylpropanesulfonic acid which has already been purified beforehand, but this leads to disadvantages. The literature describes numerous processes for preparation and for workup of the compound (A) obtained. There are also various known process routes for preparation of the salts.

A simple preparation process for compound (A) can be described by the reaction scheme which follows, in which acrylonitrile in excess as a solvent and reactant is reacted with isobutene and sulfuric acid. The sulfuric acid used may also comprise varying proportions of free $SO_3$. In one embodiment, $SO_3$ and water can also be added separately.

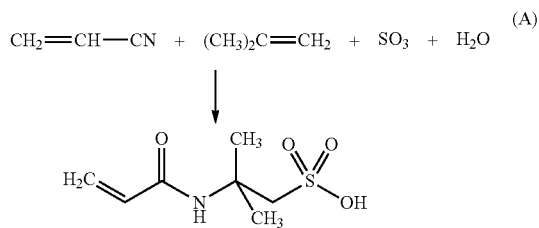

In one embodiment of the preparation process, in a continuous operation, acrylonitrile is first fed in and then admixed with isobutene and oleum. However, it is also possible to perform a batchwise process (batchwise mode).

Compound (A) is a colorless crystalline solid which is only very sparingly soluble in acrylonitrile. For the further processing, the purity of the compound (A) or salts thereof is also of particular significance because impurities in the preparation of polymers and copolymers from compound (A) or salts thereof can entail very adverse properties. More particularly, this relates to the use of compound (A) as a monomer for preparation of high molecular weight polymers and copolymers as used, for example, in mineral oil production, but also flocculants, as fluid loss polymers and as cementing polymers.

U.S. Pat. No. 4,337,215 describes a purification process for the preparation of purified 2-acrylamido-2-methylpropanesulfonic acid. The starting material in the process is a crude crystalline precipitate of AMPS which has been obtained from the reaction mixture prepared in a known manner by washing the precipitate. The crude crystals are dissolved in acetic acid comprising 5 to 40% water. The amount of aqueous acetic acid required to completely dissolve the desired amount of compound (A) at 90° C. depends on the water content. If the aqueous acetic acid has a water content of 10%, it is used in an amount of 4 to 5 times the weight of the crude crystals. The purified crystals are obtained by filtering the suspension at about 10 to 20° C.

U.S. Pat. No. 4,701,283 discloses processes for preparing compound (A) and salts thereof, and copolymer-coated solid materials and copolymer emulsions in which the copolymer is prepared by polymerizing compound (A) with another monomer.

U.S. Pat. No. 4,650,614 describes a process for purifying technical-grade 2-acrylamido-2-methylpropanesulfonic acid, which is obtained by briefly heating the sulfonic acid in a slurry with a volatile monohydric alcohol and then recovering the sulfonic acid by decanting or another form of separation and subsequently drying the solid moist sulfonic acid.

U.S. Pat. No. 6,331,647 describes the preparation and purification of acrylamidosulfonic acid monomers.

It is effected by reacting a contaminated acrylamidosulfonic acid with an aqueous solution of metal oxides or hydroxides, followed by crystallization. Disadvantages of the method are that a quantitative removal can be achieved only with high complexity due to the high solubility of the target products in water, and that a purification of the target products is made more difficult since some of the impurities crystallize out of the solution equally well or even preferentially. Particular mention should be made here of the sulfonic acids 2-methyl-2-propene-1-sulfonic acid (isobutenesulfonic acid, IBSA) and 2-methylidene-1,3-propenedisulfonic acid (isobutenedisulfonic acid, IBDSA). Thus, no high molecular weight polymers are achieved in the polymerization of compound (A) or of the sodium salt. A further principle secondary component obtained in the operation is tert-butylacrylamide (ATB).

U.S. Pat. No. 6,331,647 discloses a purification of the salt used with reference to the reduction in the peaks in an HPLC chromatogram. There is no mention of any sulfonic acids. There is likewise no discussion of the use of the purified salt for the preparation of high molecular weight polymers. It is not shown that the purification gives rise to any positive effect in use.

US-A 2010/274048 describes a process for preparing the compound (A), in which a product comprising less than 100 ppm of 2-methyl-2-propenyl-1-sulfonic acid and less than 100 ppm of 2-methylidene-1,3-propylenedisulfonic acid is obtained. The purification is effected here primarily through crystallization—subsequently, the content of the troublesome secondary components is reduced down to the desired target content by controlled washing and drying steps. Subsequently, the (A) obtained can be converted to the desired salt by reaction with bases analogously to the prior art. Another disadvantage of this process is the complex purification cycle with high capital costs.

It is an object of the present invention to provide a simple and improved process for preparing salts of compound (A) with high purity. More particularly, the content of organic impurities which have a disruptive influence in the polymerization is to be minimized.

These salts of acrylamido-2-methylpropanesulfonic acid are of significance as monomers for preparation of very high molecular weight homopolymers and copolymers. Various by-products of the preparation of compound (A) can lead to unwanted products in the polymerization.

This object is achieved by a process for preparing salts of acrylamido-2-methylpropanesulfonic acid (A) comprising the steps of:

a) preparing a solution of a contaminated salt of acrylamido-2-methyl-propanesulfonic acid (A) in an anhydrous organic solvent (L) using at least one basic component (B) selected from the group of alkali metal oxides, alkaline earth metal oxides, alkali metal hydroxides, alkaline earth metal hydroxides and amines of the general formula (I)

NR$^a$R$^b$R$^b$    (I)

where the R$^a$, R$^b$ and R$^c$ radicals are each independently: hydrogen, C$_1$-C$_4$-alkyl, hydroxy-C$_1$-C$_4$-alkyl or C$_1$-C$_4$-alkoxy, where the molar ratio of compound (A) to the basic component (B) is preferably 1:1 to 1:3, b) optionally partly removing the organic solvent (L) at a pressure in the range from 0.001 to 2 bar (abs), c) recovering the dissolved salt of compound (A) by crystallization or by precipitation, by altering the temperature and/or the pressure and/or the concentration of the salt in the solution, d) optionally drying the purified salt of acrylamido-2-methylpropanesulfonic acid (A).

The invention also relates to a process wherein the anhydrous solvent (L) used is a solvent from the group of: methanol, ethanol, propanol, butanol, acetonitrile, acetone, DMF, or a mixture of at least two of these solvents.

The invention also relates to a process wherein, in step a), an alkali metal salt of acrylamido-2-methylpropanesulfonic acid, especially the sodium salt, is used.

The invention also relates to a process wherein, in step a), a salt of acrylamido-2-methylpropanesulfonic acid (A) with an amine of the formula (I), especially a trimethylammonium salt, is used.

The invention also relates to a process wherein, in step b), at least 50% by weight of the organic solvent (L) is removed at a pressure in the range from 0.001 to 0.5 bar (abs).

The invention also relates to a process wherein, in step b), at least 60% by weight of the organic solvent (L) is removed while feeding in a gas, especially air.

The invention also relates to a process wherein, in step a), the solvent (L) used is an anhydrous C$_1$-C$_3$-alcohol, and, in step c), the purified salt is obtained from an alcoholic solution by temperature changes.

The invention also relates to a process wherein, in step c), the purified salt is obtained from the organic solution by pressure changes.

The invention also relates to a process wherein, in step c), the purified salt is obtained from the organic solution by changing the concentration and/or by adding a further organic component (NL).

The invention also relates to a process wherein at least steps a) and c) are repeated more than once. These steps (dissolution with anhydrous base, optional removal of the organic solvent and recovery of the salt) can be repeated, for example, 2 to 10 times, especially 2 to 5 times, as a result of which a higher purity can be achieved in each case.

The invention further provides acrylamido-2-methylpropanesulfonic acid (A), or a salt thereof, preparable or prepared by a process as described. The free compound (A) can be prepared from the salt.

The invention also relates to acrylamido-2-methylpropanesulfonic acid (A) or a salt with a purity of at least 99.5%, especially with a purity of at least 99.8%. Preference is given to using sodium salts, especially with a purity of at least 99.9%.

The invention also relates to the use of acrylamido-2-methylpropanesulfonic acid (A) prepared by a process as described for preparation of copolymers.

A BRIEF DESCRIPTION OF THE FIGURES

A DETAILED DESCRIPTION OF THE INVENTION

Figure 1:
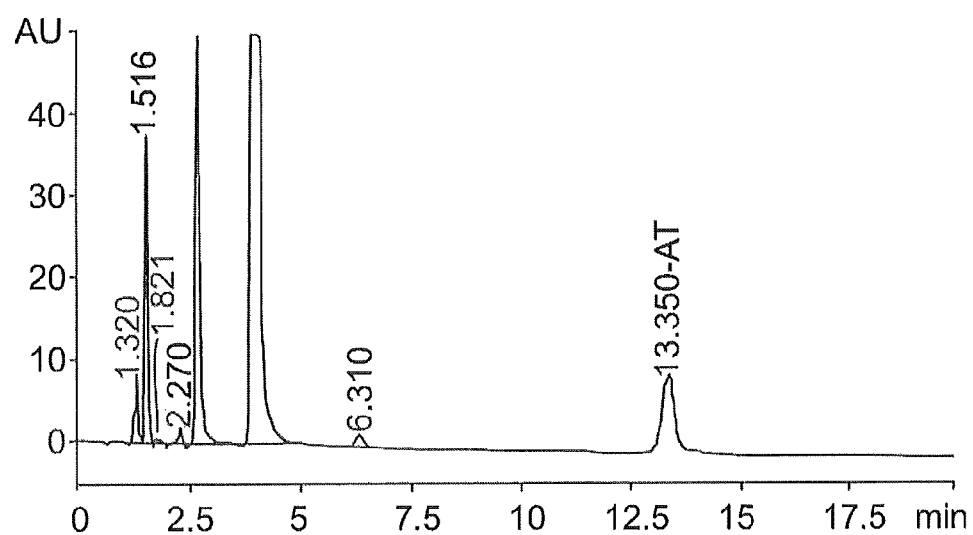
FIG. 1 shows an HPLC spectrum of the resulting product (A).

Proceeding from a contaminated compound (A), the present invention can prepare various high-purity salts of acrylamido-2-methylpropanesulfonic acid comprising only very small amounts of impurities, for example isobutenesulfonic acid (IBSA) and/or isobutenedisulfonic acid (IBDSA).

The content of these isobutenesulfonic acid (IBSA) and/or isobutenedisulfonic acid (IBDSA) by-products should preferably be a maximum of 100 ppm in total, especially a maximum of 70 ppm, preferably a maximum of 50 ppm. The invention also provides a sodium salt of compound (A) containing less than 100 ppm in total of (IBSA) and (IBDSA).

In step a) of the process, nonaqueous solutions of an alkali metal oxide or alkaline earth metal oxide, of an alkali metal hydroxide or alkaline earth metal hydroxide and/or of an organic amine of the general formula NR$^a$R$^b$R$^a$ are used. The R$^a$, R$^b$ and R$^c$ radicals are each independently hydrogen atoms, or alkyl, hydroxyalkyl or alkoxy radicals having 1 to 4 carbon atoms.

In general terms, the invention is a process for preparing and purifying the salts of compound (A), in which a nonaqueous solution or suspension of an oxide, hydroxide or amine is used. The reaction of the contaminated compound (A) with the basic component in an organic solvent gives rise to a salt.

The invention also relates to a process which is easy to implement in technical terms for obtaining a high-purity salt of compound (A), especially with a purity of greater than 99%, especially greater than 99.5%, often greater than 99.7%.

This high-purity salt is suitable as a monomer for preparation of high molecular weight copolymers or homopolymers of this monomer. The polymers prepared are suitable, inter alia, as drilling aids, flocculants, fluid loss polymers and cementing polymers.

To prepare the salts, for example, essentially organic solutions, especially alcoholic solutions, of an alkali metal oxide or alkaline earth metal oxide or alkali metal hydroxide or alkaline earth metal hydroxide or of an amine are used. The metal hydroxides of the metals of group IA and group IIA of the Periodic Table of the Elements are preferred. Specific examples of these metals are lithium, sodium, potassium, magnesium and calcium.

The particularly preferred metal of group IA is sodium, and the particularly preferred metal of group IIA is magnesium. Among the metal hydroxide solutions, preference is given to using an alcoholic solution of sodium hydroxide.

It is also possible to use a nonaqueous solution of an amine of the above-mentioned general formula NR$^a$R$^b$R$^c$. It is also possible to use an alcoholic solution of ammonia.

The expression "essentially organic solution" means in the present context that the predominant solvent (L) is organic and water is present in the solvent only to an extent not exceeding 0.5% by weight, especially not exceeding 0.2% by weight, often less than 0.1% by weight.

Suitable anhydrous organic solvents in principle are alcohols, aldehydes, ketones, nitriles, esters and ethers having 1 to 4 carbon atoms, amides such as dimethylformamide, or sulfoxides such as dimethyl sulfoxide. Preference is often given to lower alcohols.

The reaction of compound (A) with a base (B) gives a salt. There are no technical problems in the case of use of a molar excess of base (B). An excess of, for example, 1 mol % to about 20 mol % is possible. In order to achieve salt formation, the basic component (B) can be admixed with compound (A) or vice versa. The salt formation is exothermic, and the heat which arises can be used to solubilize a maximum amount of salt in the solvent. The salt solution is generally subsequently cooled and a solid salt is obtained as purified product, for example by crystallization.

The reaction of compound (A) with the base (B) to give a salt is effected at a temperature of 0° C. to 80° C. Preference is given to performing the salt formation at a temperature of about 5 to about 50° C. and especially of about 10 to about 40° C.

The molar ratio of compound (A) to base (B) in the salt formation depends on the nature of the base (B). If the base (B) is a metal of group IA, the molar ratio of (A):(B) is about 1:1 to 2, preferably 1:1 to 1.10 and especially about 1:1 to 1.05. If the base (B) is a metal of group IIA, the molar ratio of (A):(B) is about 2:1 to 2, preferably 2:1 to 1.10 and especially about 2:1 to 1.05. If the base (B) is an amine of the general formula $NR^aR^bR^c$, the ratio of moles of compound (A) to the nitrogen atoms of base (B) is about 1:1 to 2, preferably 1:1 to 1.10 and especially about 1:1 to 1.05.

The salt formed in this way is present in an organic solution. The solution can optionally be filtered to remove solid impurities. The salt of compound (A) can be recovered by subjecting the organic solution, for example, to changes in temperature and/or pressure and/or concentration.

It is also possible to add a further organic component (NL), for example a compound in which the salt of compound (A) is very sparingly soluble.

By increasing the temperature, optionally under reduced pressure, a portion of the solvent (L) is often removed, as a result of which the amount of salt present rises relative to the amount of solvent remaining. The removal of solvent at elevated temperature can be simplified by reducing the pressure. However, solvent (L) can also be removed by reducing the pressure at room temperature. By reducing the temperature, the salt is removed due to the change in solubility of the salt as a function of temperature.

In each case, the salt can be obtained by oversaturating the organic solution. Two methods for achieving such an oversaturation are changing the temperature and crystallization by stripping off the solvent. In the method of changing the temperature, a saturated solution is cooled to lower the solubility of the desired salt in the solvent (L). As a result of the lowering of the solubility, the salt crystallizes out of the solution. In the method of crystallization by stripping off the solvent, the solvent (L) is removed from the solution, either by heating or by reduced pressure, or a combination of heating and reduced pressure.

The reduced amount of solvent brings about the crystallization of the desired salt. The crystallization by changing the temperature and stripping off the solvent can be effected batchwise or continuously.

It is often advantageous that the organic solution is kept at a temperature from −20° to about 45° C. Temperatures above 45° C. can lead to rapid formation of by-products, or else to the formation of polymers. Temperatures below about −20° C. sometimes cause problems in the isolation of the salt from the organic solution.

In order to prevent polymerization, it may be helpful to use a polymerization inhibitor. Polymerization inhibitors are commercially available. A preferred polymerization inhibitor is hydroquinone monomethyl ether. In an evaporative crystallization, the solvent is distilled off under reduced pressure (less than 1 bar) to reduce the distillation temperature and to minimize by-product formation. A constant flow of a gas, for example of purge air or of another oxygen-comprising gas, can be supplied to the distillation operation.

The purity of the salts of compound (A) obtained in the process according to the invention can be determined, for example, by spectroscopic methods, for example H NMR and C-13 NMR.

Another possibility is a chromatographic removal (e.g. HPLC) of the by-products present in small amounts, which can then be determined quantitatively by means of standard methods.

The examples and claims which follow illustrate the invention.

Example 1

There follows an illustrative description of the preparation process for compound (A) in an acrylonitrile solvent on a customary laboratory scale, though the process can also be performed on a large scale:

15.5 mol (820 g) of acrylonitrile (AN) are initially charged at a temperature of −10° C., then two reaction mixing pumps are used together to supply 2.5 mol (140 g) of isobutene (boiling point is −7.1° C.) at a rate of 0.6 g/min, and 2.1 mol of oleum (205.8 g) at a rate of 22-28 ml/h. The supply takes about 3.5 h.

During the supply, the temperature rises constantly up to 2.7° C., while cooling with a thermostat (−10° C.). The end of the supply is followed by warming to a temperature of 20° C. and stirring for a period of 10 min. This forms a milky suspension of compound (A) in the excess acrylonitrile solvent, and it is also possible in some cases for residues of isobutene and $SO_3$ to be present.

The purification of compound (A) can be performed by crystallization as follows:

The described milky suspension of compound (A) in excess acrylonitrile solvent is discharged from the reaction reactor and introduced into a second reactor. The reaction reactor is rinsed once again with 550 ml of acetic acid (96%) and likewise supplied to the second redactor. The reaction mixture in the second reactor is admixed with 20 ml of water and heated under reflux (to about 87° C.). The mixture is stirred under reflux for 10 min and then cooled. The precipitated compound (A) is filtered off with suction.

The solid can be dried at 70° C. in a drying cabinet over several hours. This gives 369.4 g of compound (A), which corresponds to a yield of 85%. The product, however, still comprises several % by weight of impurities.

In the process according to the invention, in contrast, a contaminated suspension of compound (A) (obtained directly without purification or removal from the reaction of acrylonitrile, isobutene and oleum) is reacted with a substantially anhydrous solution of a base, preferably alkali metal hydroxides or alkaline earth metal hydroxides, in one or more polar solvents (L), for example methanol, ethanol, isopropanol, butanols, acetonitrile, acetone, DMF or the like. Preference is given to using an anhydrous alcohol (preferably methanol) or a mixture consisting predominantly of alcohol (preferably methanol).

A reaction with gaseous ammonia or trialkylamines as base (B) to give the corresponding ammonium salts is also possible.

The resulting solution or else suspension of the salt in the organic solvent comprises impurities which can be removed by purification methods, for example extraction or crystallization. Therefore, a preferred procedure consists in the recrystallization of the resulting sodium salt from an organic solvent or else a mixture of two or more organic solvents.

In contrast to crystallization in an aqueous system, the desired product is obtained in a relatively high purity (greater than 94%). Especially the IBSA and IBDSA impurities which lead to chain termination in the polymerization and hence to a polymer of lower molecular weight are depleted by the process according to the invention.

The same applies to a further preferred procedure in which the still-contaminated product is first filtered and then washed with an organic solvent. A product is obtained in much higher purity than in the case of performance of the same procedure in an aqueous system.

A further advantage of working in a substantially anhydrous system is that the removal of the solvent or of the solvent mixture is distinctly simplified. The product is also obtained in a crystalline form which is easy to filter. It can be dried in a simple manner. In contrast, a crystallization from an aqueous system gives a product which is much harder to filter. The drying is also complex.

Example 2

Preparation of the Sodium Salt of Compound (A) (NaATBS, Anhydrous) Directly from the Reaction Mixture Acrylonitrile, isobutene and oleum were reacted with one another as described above to give an about 25% suspension of crystalline ATBS in acrylonitrile.

This solution was admixed at 5° C. in a controlled manner with a solution of NaOH in dry methanol (18% NaOH in MeOH) until pH=7.8 was attained. This gave a homogeneous, pale yellowish solution with an NaATBS content of approx. 16.7% by weight (determination by calibrated HPLC), which was processed further directly.

Example 3

Preparation of NaATBS from a Substantially Anhydrous System

About 50 g of solvent were removed at room temperature under reduced pressure and while introducing air into the reaction solution from 100 g of a solution, obtained according to example 1, of NaATBS (16.77% by weight) in acrylonitrile and methanol. This gave a suspension of colorless, readily filterable NaATBS. The product was separated from the residual solvent by filtration and washed with further acrylonitrile/methanol. This left 17.3 g of slightly contaminated, finely crystalline NaATBS (purity 94%). The proportion by weight of IBSA was 0.43%, the proportion by weight of ATB 1.7%.

FIG. 1 shows an HPLC spectrum of the resulting product (A). It is evident in the HPLC spectrum that numerous unwanted secondary components, for example tert-butylacrylamide, acrylonitrile, IBSS and IBDSS, are also present. It is thus difficult to obtain a polymer with sufficiently high molecular weight from the polymerization of such a product. The abscissa of the HPLC spectrum shows the time (0 to 17.5 minutes), the ordinate the intensity.

Example 4

Purification of NaATBS by Crystallization from Organic Solvents (Substantially Anhydrous Reaction Regime)

About 503 g of distillate were removed under reduced pressure and while introducing air into the reaction solution from 809 g of a solution, obtained according to example 1, of NaATBS (16.77% by weight) in acrylonitrile and methanol. 383 g of acetone were added to the remaining 306 g of solution and the mixture was cooled to 0° C. After a period of 15-20 min, NaATBS began to precipitate in the form of white crystals. The resulting precipitate was removed by filtration, washed with acetone and dried cautiously at 70° C. This gave purified NaATBS of purity >>95%, which no longer comprised any ATB and in which the proportion of IBSA had been reduced to 0.3% by weight. Repeated use of the method (recrystallization, washing) and drying at 110° C. led to NaATBS of high purity which was suitable for the preparation of polymers of high molecular weight.

Figure 2:
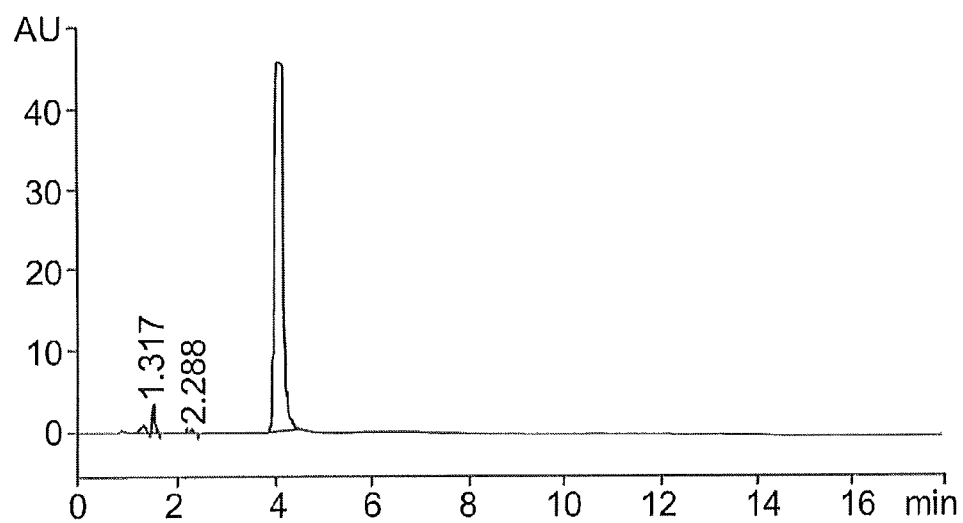
FIG. 2 shows an HPLC spectrum of the resulting product (A).

FIG. 2 shows an HPLC spectrum of the resulting product (A). It is evident in the HPLC spectrum that the level of unwanted secondary components has been distinctly reduced. More particularly, the IBSS and IBDSS secondary components which are troublesome in the polymerization of monomer (A) have been reduced to <100 ppm. The abscissa of the HPLC spectrum shows the time (0 to 16 minutes), the ordinate the intensity.

Figure 3:
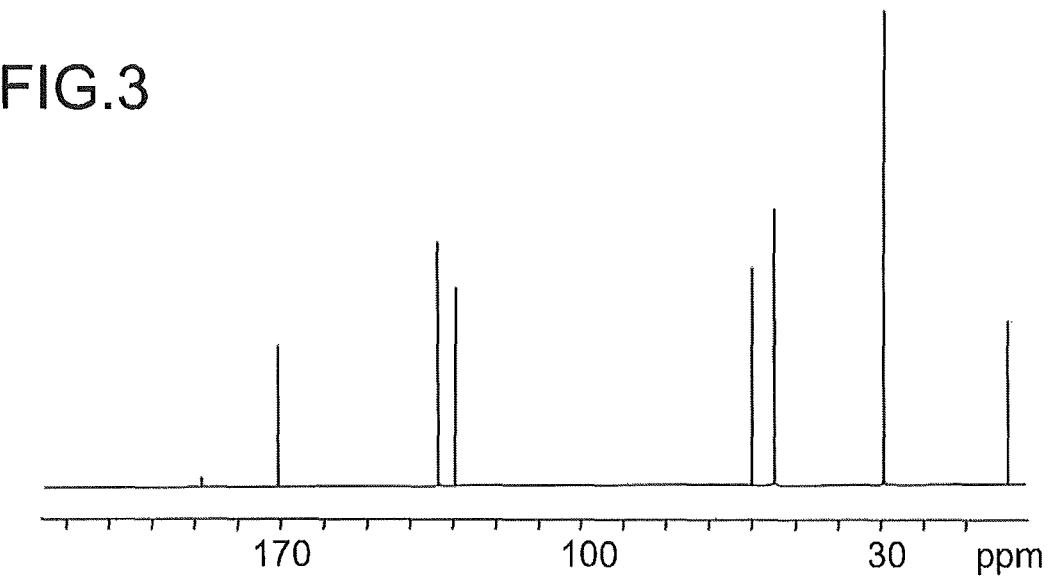
FIG. 3 shows an HPLC spectrum of the resulting product (A).

FIG. 3 shows an NMR spectrum of the resulting product (A). It is evident in the NMR spectrum that the resulting product has a very high purity. The abscissa of the NMR spectrum shows the shift (220 to 0 ppm) and the type of signal (s, d, t or q). Such a purified salt of compound (A) is suitable for preparation of polymers of high molecular weight.

Comparative Example 1

Crystallization of Sodium Salt of Compound (A) NaATBS from Water (Analogously to U.S. Pat. No. 6,331,647)

100 g of water were removed under reduced pressure and while introducing air into the reaction solution from 440 g of a 50% solution of NaATBS in water.

A viscous, honeylike precipitate was obtained, which was separable from the filtrate by filtration only with difficulty. The filtercake was dried at 35° C. under reduced pressure. By repeating the procedure several times, a total of 224 g of slightly contaminated NaATBS (purity 94%) was obtained, which, after drying, was present as an amorphous solid. The proportion by weight of IBSA was 0.43%—thus, a salt of compound (A) obtained in such a way is unsuitable for achieving polymers of high molecular weight. The salt of compound (A) also comprised 4-5% by weight of water of crystallization, which could not be removed from the solid even by drying.

Comparative Example 2

Purification of Salt of Compound (A) NaATBS by Crystallization from Aqueous Solution with Organic Solvents 200 g of an about 50% solution of NaATBS in water (stabilized with 100 ppm of MEHQ, proportion by weight of IBSA approx. 0.4%) was admixed with 400 ml of acetone at 20° C. while stirring.

This gave a fine white precipitate which was removed from the mother liquor by filtration. After cautious drying at 70° C., the solid was analyzed by calibrated HPLC. This gave a purity of NaATBS of 84.8% by weight with a proportion by weight of IBSA of 3.9%. This procedure thus enriched the unwanted IBSA secondary component. Thus, the resulting product (A) (NaATBS) is unsuitable for achieving polymers with high molecular weight.

Figure 4:
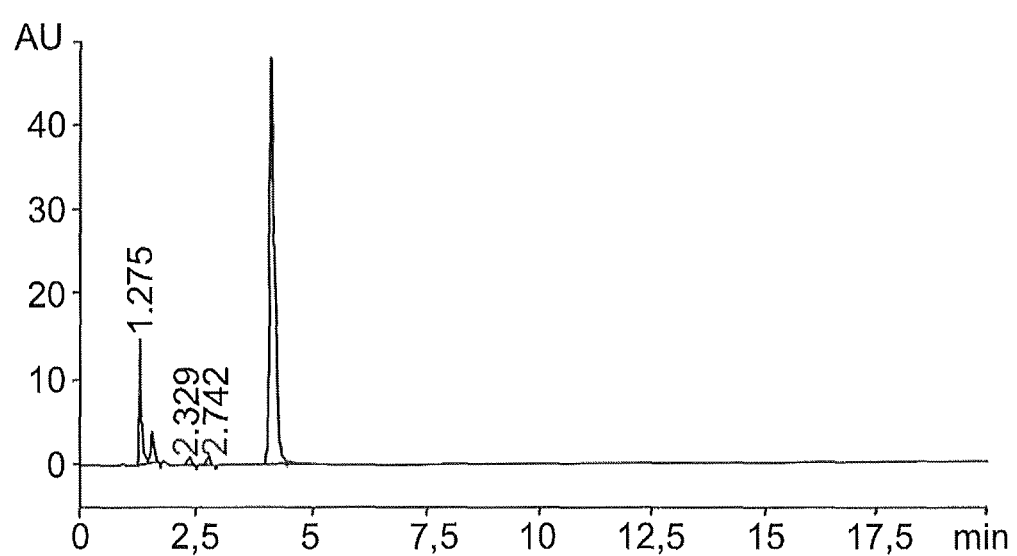
FIG. 4 shows an HPLC spectrum of the resulting product (A).

FIG. 4 shows an HPLC spectrum of the resulting product (A). It is evident in the HPLC spectrum that numerous unwanted secondary components, for example tert-butylacrylamide, acrylonitrile, IBSS and IBDSS, are present. The abscissa of the HPLC spectrum shows the time (0 to 17.5 minutes), the ordinate the intensity. Thus, it is not possible to obtain a polymer with sufficiently high molecular weight from the polymerization of such a product.

The invention claimed is:

1. A process for preparing salts of acrylamido-2-methylpropanesulfonic acid (A) comprising the steps of:
    a) preparing a solution of a contaminated salt of acrylamido-2-methylpropanesulfonic acid (A) in an anhydrous organic solvent (L) using at least one basic component (B) selected from the group of alkali metal oxides, alkaline earth metal oxides, alkali metal hydroxides, alkaline earth metal hydroxides and amines of the general formula (I)

$NR^a R^b R^c$         (I)

where the $R^a$, $R^b$ and $R^c$ radicals are each independently: hydrogen, $C_1$-$C_4$-alkyl, hydroxy-$C_1$-$C_4$-alkyl or $C_1$-$C_4$-alkoxy,
    b) optionally partly removing the anhydrous organic solvent (L) at a pressure in the range from 0.001 to 2 bar (abs),
    c) recovering the dissolved salt of compound (A) by crystallization or by precipitation, by altering the temperature and/or the pressure and/or the concentration of the salt in the solution,
    d) optionally drying the purified salt of acrylamido-2-methylpropanesulfonic acid (A),
    wherein the anhydrous organic solvent (L) is selected from the group consisting of methanol, ethanol, propanol, butanol, acetonitrile, acetone, DMF and a mixture of at least two of methanol, ethanol, propanol, butanol, acetonitrile, acetone and DMF.

2. The process according to claim 1, wherein, in step a), an alkali metal salt of acrylamido-2-methylpropanesulfonic acid is used.

3. The process according to claim 1, wherein, in step a), a salt of acrylamido-2-methylpropanesulfonic acid (A) with an amine of the formula (I) is used.

4. The process according to claim 1, wherein, in step b), at least 50% by weight of the organic solvent (L) is removed at a pressure in the range from 0.001 to 0.5 bar (abs).

5. The process according to claim 1, wherein, in step b), at least 60% by weight of the organic solvent (L) is removed while feeding in a gas.

6. The process according to claim 1, wherein, in step a), the solvent (L) used is an anhydrous $C_1$-$C_3$-alcohol, and, in step c), the purified salt is obtained from an alcoholic solution by temperature changes.

7. The process according to claim 1, wherein, in step c), the purified salt is obtained from the organic solution by pressure changes.

8. The process according to claim 1, wherein, in step c), the purified salt is obtained from the organic solution by changing the concentration and/or by adding a further organic component (NL).

9. The process according to claim 1, wherein at least steps a) and c) are repeated more than once.

10. A process for the preparation of copolymers which comprises utilizing the acrylamido-2-methylpropanesulfonic acid (A) or salt thereof, prepared by the process according to claim 1.

11. The process according to claim 1, wherein, in step a), a sodium salt of acrylamido-2-methylpropanesulfonic acid is used.

12. The process according to claim 1, wherein, in step a), a salt of acrylamido-2-methylpropanesulfonic acid (A) with a trimethylammonium salt, is used.

13. The process according to claim 1, wherein, in step b), at least 60% by weight of the organic solvent (L) is removed while feeding in air.

14. The process according to claim 1, where, in step a), the molar ratio of compound (A) to the basic component (B) is 1:1 to 1:3.

* * * * *